US011453125B2

(12) United States Patent
Silverstein et al.

(10) Patent No.: US 11,453,125 B2
(45) Date of Patent: Sep. 27, 2022

(54) DRONE-ENABLED ACTIVE FALL PROTECTION

(71) Applicant: KYNDRYL, INC., New York, NY (US)

(72) Inventors: Michael Seth Silverstein, Jacksonville, FL (US); Todd Russell Whitman, Bethany, CT (US); Zachary A. Silverstein, Jacksonville, FL (US); Michael Bender, Rye Brook, NY (US); Jeremy R. Fox, Georgetown, TX (US)

(73) Assignee: KYNDRYL, INC., New York, NY (US)

( * ) Notice: Subject to any disclaimer, the term of this patent is extended or adjusted under 35 U.S.C. 154(b) by 275 days.

(21) Appl. No.: 16/813,593

(22) Filed: Mar. 9, 2020

(65) Prior Publication Data

US 2021/0276189 A1 Sep. 9, 2021

(51) Int. Cl.
*B25J 9/16* (2006.01)
*G05D 1/00* (2006.01)
(Continued)

(52) U.S. Cl.
CPC .......... *B25J 9/1674* (2013.01); *A61B 5/1117* (2013.01); *A62B 35/0068* (2013.01); *B25J 9/162* (2013.01);
(Continued)

(58) Field of Classification Search
CPC ........ B25J 9/1674; B25J 9/162; B25J 9/1661; B25J 9/1679; B25J 11/00; B25J 11/008;
(Continued)

(56) References Cited

U.S. PATENT DOCUMENTS 8,505,683 B1 * 8/2013 Dirrig ................... A63B 27/00
                                                              182/9
8,909,391 B1    12/2014 Peeters
                        (Continued)

FOREIGN PATENT DOCUMENTS

DE    102018001627 A1    9/2019
KR       101757368 B1    7/2017

OTHER PUBLICATIONS

"Aerialtronics Commercial Drones Give IBM Watson Internet of Things a Bird's Eye View", 5 pps., Oct. 3, 2016, IBM, <https://www-03.ibm.com/press/us/en/pressrelease/50688.wss>.

(Continued)

*Primary Examiner* — Abby Y Lin
*Assistant Examiner* — Sohana Tanju Khayer
(74) *Attorney, Agent, or Firm* — Erik Swanson; Andrew M. Calderon; Roberts Calderon Safran & Cole P.C.

(57) ABSTRACT

A method for providing active fall prevention assistance to a user. The method includes one or more computer processors mapping a work area where a user performs a plan of tasks. The method further includes determining a safety configuration related to the user and the task. The method further includes instructing an autonomous device to attach a first tether between a first anchor point and a safety harness secured to the user. The method further includes analyzing real-time images of the work area and the user while the user performs the task. The method further includes determining that the user is at risk of falling. The method further includes responding to determining that the user is at risk of falling by instructing the autonomous device to attach a second tether between a second anchor point and the safety harness secured to the user.

20 Claims, 5 Drawing Sheets

(51) Int. Cl.
 A61B 5/11 (2006.01)
 B25J 11/00 (2006.01)
 A62B 35/00 (2006.01)
(52) U.S. Cl.
 CPC ........... *B25J 9/1661* (2013.01); *B25J 9/1679* (2013.01); *B25J 11/00* (2013.01); *B25J 11/008* (2013.01); *G05D 1/0055* (2013.01); *G05D 1/0094* (2013.01); *B25J 9/1697* (2013.01)
(58) Field of Classification Search
 CPC .... B25J 9/1697; A61B 5/1117; A61B 5/0022; A61B 5/1128; A61B 5/7275; A62B 35/0068; G05D 1/0055; G05D 1/0094
 See application file for complete search history.

(56) References Cited

U.S. PATENT DOCUMENTS

| | | | | |
|---|---|---|---|---|
| 2011/0047764 | A1* | 3/2011 | Strasser | F16B 45/021 24/599.5 |
| 2011/0103558 | A1* | 5/2011 | Hooten | A62B 35/04 379/37 |
| 2012/0152654 | A1* | 6/2012 | Marcus | A62B 5/00 182/129 |
| 2013/0233648 | A1* | 9/2013 | Smit | A62B 35/0043 182/241 |
| 2015/0217150 | A1* | 8/2015 | Harris | A01M 31/02 182/5 |
| 2016/0354621 | A1* | 12/2016 | Moore, Jr. | A62B 35/0075 |
| 2019/0025822 | A1 | 1/2019 | Sentosa | |
| 2019/0046816 | A1 | 2/2019 | Browning | |
| 2020/0376343 | A1* | 12/2020 | Dickenson | A62B 35/0043 |

OTHER PUBLICATIONS

"Condition, Not Time, Determines When to Replace Your Personal Fall Protection Equipment", Jan. 22, 2018, Rigid Lifelines, Fall Protection Forum, 5 pps., <https://www.rigidlifelines.com/blog/entry/condition-not-time-determines-when-to-replace-your-personal-fall-protection>.
"FAA Aerospace Forecast Fiscal Years 2019-2039", Federal Aviation Administration, printed from the Internet on Jan. 13, 2020, 107 pps., <https://www.faa.gov/data_research/aviation/aerospace_forecasts/media/FY2019-39_FAA_Aerospace_Forecast.pdf>.
"Rock climbing", From Wikipedia, the free encyclopedia, last edited on Jan. 3, 2020, 15 pps., <https://en.wikipedia.org/wiki/Rock_climbing>.
"The Future of Drones According to the AT&T Foundry", RocketSpace, printed from the Internet on Jan. 13, 2020, 52 pps., <http://www.rocketspace.com/drones>.
Addison, Nov. 12, 2014, "Installing & Inspecting Your Permanent Roof Anchors", Rigid Lifelines, Fall protection Forum, 8 pps., <https://www.rigidlifelines.com/blog/entry/installing-inspecting-your-permanent-roof-anchors#>.
Carmel, "Eyes in the Sky: Drone Inspection for Smarter Operations in Government", the Internet of Things blog, Apr. 8, 2019, 4 pps., <https://www.ibm.com/blogs/internet-of-things/iot-drone-inspection-for-smarter-operations-in-government.
Cassano, "This Automatic Parachute Keeps Your Drone From Crashing And Burning", May 27, 2015, Fasy Company, 7 pps., <https://www.fastcompany.com/3046653/this-automatic-parachute-keeps-your-drone-from-crashing-and-burning>.
Ferranti, "IBM's Watson IoT hits the skies with Aerialtronics drone deal", Computerworld, Sep. 16, 2016, 5 pps., <https://www.computerworld.com/article/3121224/ibms-watson-iot-hits-the-skies-with-aerialtronics-drone-deal.html>.
Frangoul, "IBM announces partnerships to monitor worker safety", Feb. 14, 2019, CNBC, 4 pps., <https://www.cnbc.com/2019/02/14/ibm-announces-partnerships-to-monitor-worker-safety-.html>.
Galarreta et al., "UAV-based urban structural damage assessment using object-based image analysis and semantic reasoning", Nat. Hazards Earth Syst. Sci., 15, 1087-1101, 2015, <https://www.nat-hazards-earth-syst-sci.net/15/1087/2015/nhess-15-1087-2015.pdf>.
Greenstein, "It's a bird, it's a plane, it's Watson IoT!", Oct. 3, 2016, IBM, Internet of Things blog, 9 pps., <https://wwww.ibm.com/blogs/internet-of-things/cognitive-announcement-aerialtronics-drones/>.
Iuga et al., "Fall monitoring and detection for at-risk persons using a UAV", 6 pps., printed from the Internet on Jan. 13, 2020, <https://www.sciencedirect.com/science/article/pii/S2405896318305834>.
Lee et al., "Diagnosis of crack damage on structures based on image processing techniques and R-CNN using unmanned aerial vehicle (UAV)", SPIE. Digital Library, Mar. 27, 2018, Proceedings vol. 10598, Sensors and Smart Structures Technologies for Civil, Mechanical, and Aerospace Systems 2018; 1059811 (2018), 21 pps., <https://www.spiedigitallibrary.org/conference-proceedings-of-spie/10598/1059811/Diagnosis-of-crack-damage-on-structures-based-on-image-processing/10.1117/12.2296691.short?SSO=1>.
Miller, "The Cost of a Poor Safety Program", Sep. 17, 2018, Rigid Lifelines, Fall Protection Forum, Sep. 17, 2018, 8 pps., <https://www.rigidlifelines.com/blog/entry/the-cost-of-a-poor-safety-program>.
O'Connor, "The cognitive drone and the promise of IoT", IBM, the Internet of Things Blog, Jun. 1, 2017, 11 pps., <https://www.ibm.com/blogs/internet-of-things/iot-cognitive-drone/>.

* cited by examiner

DRONE-ENABLED ACTIVE FALL PROTECTION

BACKGROUND OF THE INVENTION

The present invention relates generally to the field of automated safety devices, and more particularly to utilizing autonomous devices to prevent accidents within a work area.

Generally speaking, a drone is autonomous (or semi-autonomous) device and is usually an electro-mechanical machine that is guided by a computer program and/or electronic circuitry. Unmanned autonomous devices may range in form from unmanned vehicles tailored to specific environments, such as unmanned aerial vehicles (UAVs), unmanned surface vehicles (USVs), unmanned underwater vehicles (UUVs), etc.; to non-vehicular devices, such as humanoids robots; insectoid robots, crawlers with gripping appendages, collectively programmed swarm robots (e.g., bots), etc. Various type of autonomous devices include sensors and/or cameras that enable an autonomous device to at least detect and avoid obstacles and negotiate a path of movement. Some autonomous devices also include more sophisticated electronics, hardware, and software to enable the autonomous device to identify and react to objects and features within the environment where the autonomous device operates.

Internet of Things (IoT) is defined as the ability of various physical devices and every-day objects to be connected to each other through the Internet. Embedded with electronics, Internet connectivity, and other forms of hardware (such as sensors), IoT devices can communicate and interact with others over the Internet, a wireless network, and other inter-device communication methods such that the IoT devices can provide information and be remotely monitored/controlled. IoT devices can include human-to-device communication. For example, a user may verbally command an IoT device or IoT-enabled device to perform various actions, such as vacuum a room, identify occupants within an area, identify weather conditions, detect a package delivery, etc. In addition, IoT devices can determine information about the surroundings within a proximity of the IoT devices, periodically or in real-time, and store the data for later access by a user.

SUMMARY

According to an aspect of the present invention, there is a method, computer program product, and/or system for active fall prevention assistance to a user. In an embodiment, the method includes at least one computer processor mapping a work area where a user performs a plan of tasks. The method further includes at least one computer processor determining a safety configuration related to the user and the task. The method further includes at least one computer processor instructing an autonomous device to attach a first tether between a first anchor point and a safety harness secured to the user. The method further includes at least one computer processor analyzing real-time images of the work area and the user while the user performs the task. The method further includes at least one computer processor determining that the user is at risk of falling. The method further includes at least one computer processor responding to determining that the user is at risk of falling by instructing the autonomous device to attach a second tether between a second anchor point and the safety harness secured to the user.

DETAILED DESCRIPTION

Figure 1:
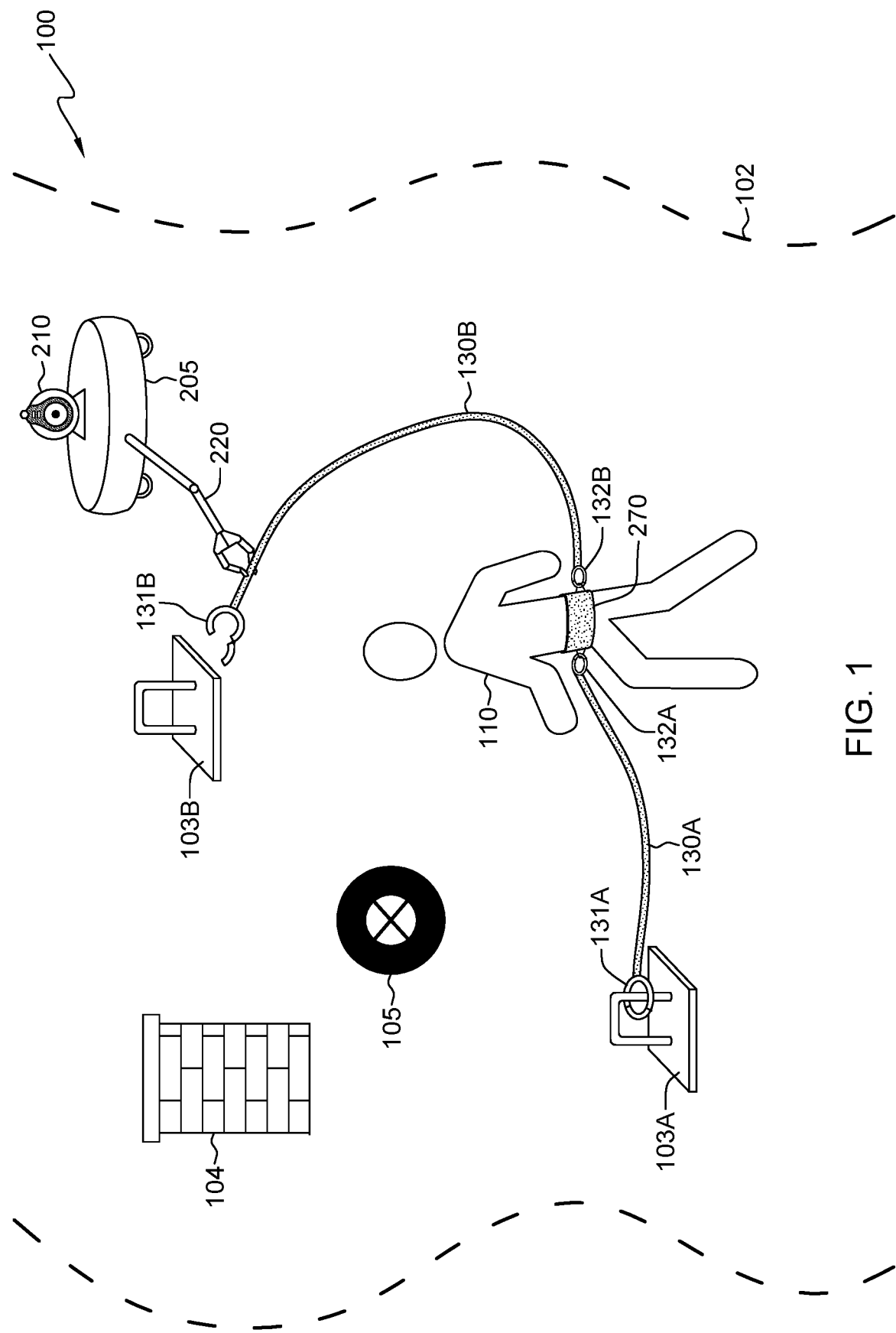
FIG. 1 is an illustrative example depicting an environment for providing a user assistance to prevent or mitigate a fall by the user within a work area, in accordance with an embodiment of the present invention.

Embodiments of the present invention recognize that falling presents tremendous risk to both the commercial and consumer industries. Physical repairs or work on buildings and other structures, of any significant height, can present a serious fall risk, expose a business or individual to significant liability, and drive costs associated with workers' compensation insurance. For example, one 2018 Safety Index study estimated the workers' compensation costs for a combination of all types of falls at over $10 billion dollars. Embodiments of the present invention recognize that some current solutions manually secure a worker with harnesses and at least one rope (e.g., tether) attached to anchor points within a work area to provide safety. Such manual practices rely on workers securing (e.g., tying) themselves to an anchor point that a worker believes is strong enough to support the worker while performing various tasks. However, manually safety measures to mitigate falling risks are a balancing act between worker safety and the mobility associated with the worker to perform required tasks within a work area.

Embodiments of the present invention also recognize that information related to a portion of a work area may be limited to what the worker can see at a point in time or a vantage point within the work area; thus, preventing the worker from identifying and utilizing other potential anchor points. Embodiments of the present invention also recognize that a worker may not know the strength (e.g., load-bearing capacity) of an anchor point and/or may have to execute unsafe movements to access and anchor point or detach from an anchor point. In addition, embodiments of the present invention further recognize that not all portions of a work area have the same structural strength nor are as safe to traverse, such as narrow beams, sloping surfaces, surfaces with differing traction characteristics, etc.

Embodiments of the present invention utilize various technologies, such as one or more autonomous devices that include machine vision and mechanical manipulation capabilities, Internet-of-Things (IoT)-enabled devices, and various physical safety devices and hardware to actively assist a user performing tasks within the work area to improve the safety, such as fall prevention and/or fall mitigation related to a user. Falls includes short distances (e.g., less than a user's height) falls within a work area and more dangerous long-distance falls where the user exits the work area or experiences g-forces forces related a sudden and unexpected change of elevations within the work area. For example, an embodiment of the present invention utilizes one or more autonomous devices to secure one or more anchor points (e.g., attachment locations) prior to the user beginning a plan of tasks within the work area. In response to a user entering the mapped work area to perform a planned task an autonomous device secures a tether to an anchor point and secures the other end of the tether to a safety harness worn by the user.

Embodiments of the present invention map a work area, identify safety factors, determine a safety strategy for executing a plan of tasks within the work area, and determine configurations of safety hardware to provide active safety assistance to user while performing the plan of tasks within the work area. In an example, embodiments of the present invention utilize machine vision, image recognition, and/or one or more sensors while mapping a work area to identify actual or potential anchor points where safety equipment (e.g., tethers) can be attached; identify obstacles, hazards, unsafe areas, and/or other safety factors within the work area; and determine a set of safety configurations (i.e., a safety strategy) related to the tasks planned for the work area and one or more users that perform the planned tasks. Some embodiments of the present invention enable two or more autonomous devices to cooperate, share information and resources, and/or support a plan of tasks within a work area that requires two or more users.

Other embodiments of the present invention actively monitor the user while performing the planned tasks within the work area and dynamically modify a safety configuration related to the user based on the movements of the user and the tasks that the user is planned to perform within the work area. Further embodiments of the present invention utilize cognitive functions, external information, and predictive analytics to identity variations among the performed tasks and/or movements of the user within the work area. Additional embodiments of the present invention can respond to changes by dynamically modifying a safety strategy related to the user and the work area, such as responding to a weather change or detecting an unsafe condition (e.g., a structural weakness) that develops within the work area while the user performs planned tasks. Another embodiment of the present invention can include hazards within a safety strategy and devise safety configurations that prevent the user from approaching a hazard in addition to preventing and/or mitigating falls. Or alternatively, determining a safety configuration that constrains a user, should a fall occur, to towards the least unsafe portion of the work area.

The descriptions of the various scenarios, instances, and examples related to the present invention have been presented for purposes of illustration but are not intended to be exhaustive or limited to the embodiments disclosed.

The present invention will now be described in detail with reference to the Figures. FIG. 1 is diagram depicting an environment 100 for providing a user safety assistance within a work area. In an embodiment environment 100 includes work area 102; element 103A and element 103B, defined anchor points; element 104, a structure-based anchor point; element 105, a dynamically-created anchor point; user 110; tether 130A and tether 130B, which further include respective anchor point connectors 131A and 131B, and respective safety harness connectors 132A and 132B; autonomous safety device (ASD) 205; and safety harness 270 secured to user 110. In some embodiments, environment 100 includes a different number of one or more elements, such as multiple instances of ASD 205, and/or two or more instance of user 110 to performs a plan of tasks within work area 102. Various items or features within environment 100 and/or work area 102 are discussed in further detail with respect to FIG. 2.

Work area 102 can be an area on, around, and/or within: a residence, a building, a construction area, a disaster area, or a natural environment that includes conditions that contribute to falling-type accidents and/or situations for a user performing tasks within work area 102. For example, work area 102 may represent a pitched roof; a side of a building; a framework associated with a structure, such as exposed internal structural components or a scaffolding; a framework that is the structure, such as a utility tower, etc. In some embodiments, work area 102 includes a number of elements different from the number of elements depicted in FIG. 1, such as zero instances of element 105, two instances of element 104, a plurality of defined anchor points (e.g., instances of element 103A and/or element 103B), etc.

In an embodiment, some instances element 104 within environment 100 represents elements within a proximity of work area 102, such as scaffolding, or a fire escape attached to a structure. In various embodiments, work area 102 can include a plurality of other elements and/or hazards (not shown), such as surfaces at differing angles, obstacles, open areas, areas of damage, exposed utilities, moving objects, features with minimal load-bearing capacity, etc.

In an embodiment, element 103A and element 103B represent a plurality of instances of a defined anchor point. In illustrative environment 100 element 103A and element 103B depict an anchor point that includes a plate with a square loop or other projection and are secured to one or more surfaces within work area 102. The shape of element 103A and element 103B has been chosen for the purpose of explaining embodiments of the present invention and is not to be construed as a limiting example. Other types and configurations related to element 103A and/or element 103B may include a bayonet mount, a quick disconnect coupling, etc. In some embodiments, additional instances of element 103A and/or element 103B are affixed within work area 102 by ASD 205 in response to executing safety monitoring program 400.

Element 104 represents a portion of a structure, an item secured to work area 102, or an item in proximity to work area 102 that can support forces associated with securing user 110 within work area 102, such as weight, lateral loads, etc. In one embodiment, element 104 represents a structure-based anchor point that a tether, such as tether 130B loops around and slides over another portion of the tether 130B via an anchor point connector 131B. In another embodiment, element 104 represents a structure-based anchor point, such as a fire escape that a tether (not shown) can attach to via an applicable anchor point connector, such as a grapnel.

Element 105 is representative of one or more dynamical-created anchor points that are installed within or secured to a surface of work area 102 by ASD 205. An instance of element 105 may include a magnetic plate, pigtail eyebolts, or a type of anchor point previously discussed with respect to element 103A and element 103B. In an embodiment, safety monitoring program 400 determines to create one or more additional anchor point within work area 102 based on monitoring user 110. Subsequently, safety monitoring program 400 instructs ASD 205 to secure an applicable instance element 105 at a dictated location. In another embodiment, an instance of element 105 represents a defined anchor point (e.g., element 103A) that is created or moved after executing safety planning program 300 but before user 110 begins a plan of tasks based on one or more changes associated with work area 102, such as a change in the weather.

In an embodiment, tethers 130A and 130B are representative of a flexible or semi-flexible item of safety hardware. In an embodiment, tether 130A and tether 130B include respective anchor point connectors 131A and 131B, and respective safety harness connectors 132A and 132B. In one embodiment, tether 130A and tether 130B are selected to be compatible to attach to elements 103A and 103B. In some embodiments, tether 130A and/or tether 130B include additional features described in further detail with respect to FIG. 2 (i.e., tether 130).

In an embodiment, user 110 performs one or more tasks of a plan of tasks within work area 102. As used herein a user can refer to an individual (e.g., a homeowner), a worker, a contractor, an emergency responder, or any other personnel performing tasks and actions within a work area. In one embodiment, user 110 is wears safety harness 270, which is further secured to anchor points (i.e., elements 103A and 103B) via tether 130A and tether 130B utilizing respective anchor point connectors 131A and 131B. In some embodiments, safety harness 270 includes additional features described in further detail with respect to FIG. 2.

ASD 205 is an autonomous safety device that maps work area 102, monitors user 110 performing a plan of tasks related to work area 102 utilizing at least camera 210. The shape of ASD 205 has been chosen for the purpose of explaining embodiments of the present invention and is not to be construed as a limiting example. In addition, ASD 205 utilizes camera 210, mechanical manipulator 220, and other features (described in further detail with respect to FIG. 2) to provide active safety assistance to user 110 while performing the plan of tasks, such as traversing work area 102 to attach tether 130B from safety harness 270 to element 103B utilizing anchor point connector 131B.

Figure 2:
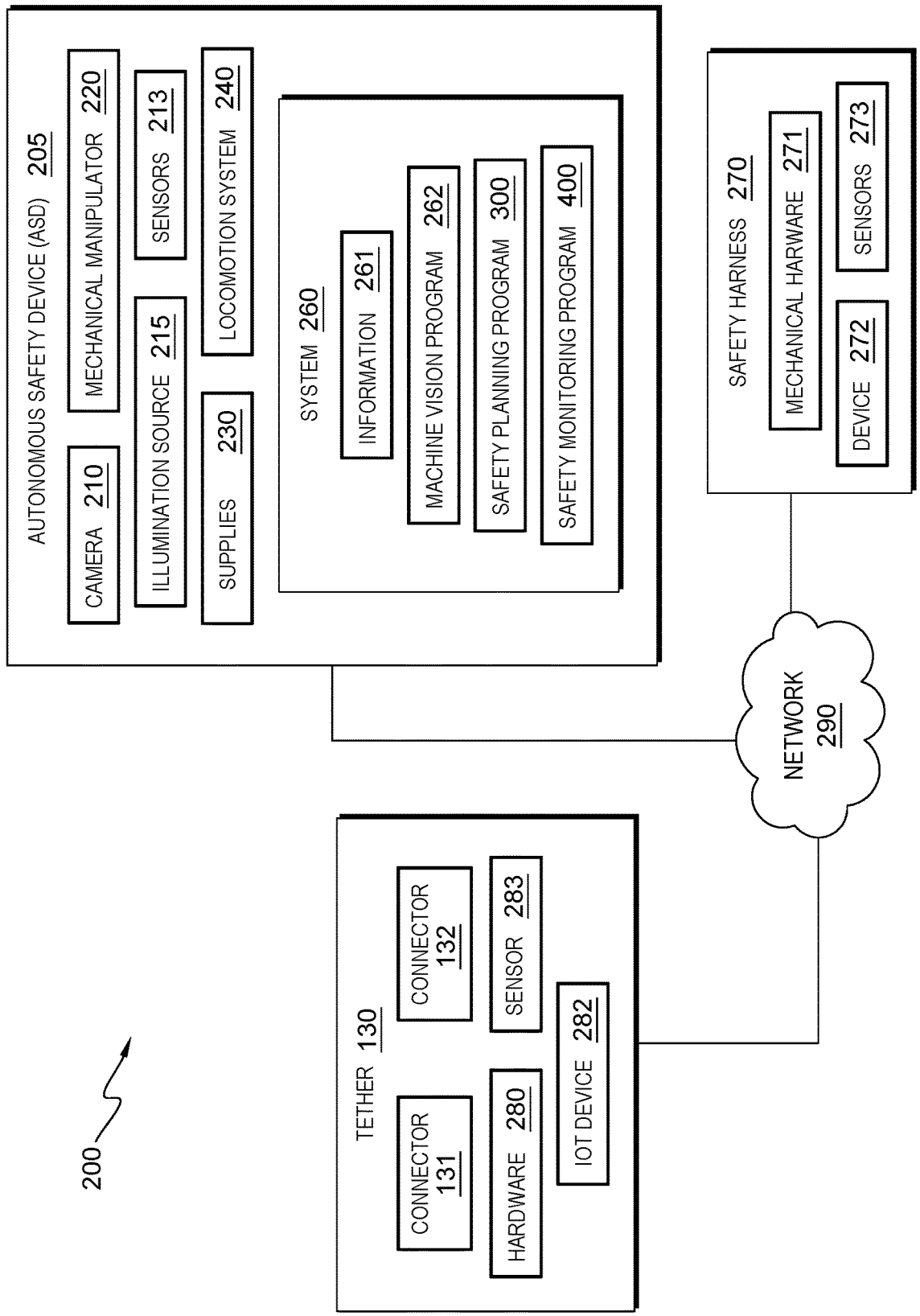
FIG. 2 is a block diagram depicting a computing environment for providing a user safety assistance within a work area, in accordance with an embodiment of the present invention.

FIG. 2 is a block diagram illustrating computing environment 200 for mapping a work area and providing safety assistance to the user while the user is performing tasks within the mapped work area, in accordance with embodiments of the present invention. In an embodiment, computing environment 200 includes ASD 205, at least one instance of IoT-enabled tether 130, and device 272, all interconnected over network 290. In some embodiments, computing environment 200 an IoT-enabled instance of safety harness 270. In various embodiments, one or more elements of computing environment 200 can utilize network 290 to access other information and computing resources (not shown), such as the Internet. It is to be understood that the functional division of components of computing environment 200 have been chosen for the purpose of explaining embodiments of the present invention and is not to be construed as a limiting example.

System 260 and device 272 may be laptop computers, tablet computers, netbook computers, personal computers, personal digital assistants (PDA), smart phones, embedded microcontrollers, wearable devices (e.g., smart glasses, smart watches, e-textiles, AR headsets, etc.), or any programmable computer systems known in the art. In some embodiments, device 272 is an IoT device. In general, system 260, device 272, and IoT device 282 are representative of any programmable electronic device or combination of programmable electronic devices capable of executing machine readable program instructions and communicating via network 290. System 260, device 272, and instances of IoT device 282 may include components, as depicted and described in further detail with respect to FIG. 5, in accordance with embodiments of the present invention.

Various embodiments of the present invention may utilize various data sources, such as information 261, that may include personal data, content, or information the user wishes not to be processed. Personal data includes personally identifying information or sensitive personal information as well as user information, such as tracking or geolocation information. Processing refers to any, automated or unautomated, operation or set of operations such as collection, recording, organization, structuring, storage, adaptation, alteration, retrieval, consultation, disclosure by transmission, dissemination, use, or otherwise making available, combination, restriction, erasure, or destruction performed on personal data. Safety planning program 300 and/or safety monitoring program 400 also enable the authorized and secure processing of personal data. Safety planning program 300 and/or safety monitoring program 400 provide informed consent, with notice of the collection of personal data, allowing the user to opt in or opt out of processing personal data. Consent can take several forms. Opt-in consent can impose on the user to take an affirmative action before personal data is processed. Alternatively, opt-out consent can impose on the user to take an affirmative action to prevent the processing of personal data before personal data is processed. Safety planning program 300 and/or safety monitoring program 400 provide information regarding personal data and the nature (e.g., type, scope, purpose, duration, etc.) of the processing. Safety planning program 300 and/or safety monitoring program 400 provide the user with copies of stored personal data. Safety planning program 300 and/or safety monitoring program 400 allow the immediate deletion of personal data.

Tether 130 represents a safety device that includes one or more types of flexible or semi-flexible materials to attach to safety harness 270, secured to user 110, and at least one anchor point within work area 102. An instance of tether 130 can be a rope, a cable (e.g., wire rope), a chain, a strap, a segment of webbing, etc. Tether 130 can be of a static or a dynamic material construction and may be further identified by one or more performance, strength, fall factor, or load-bearing ratings. In an embodiment, an instance of tether 130 includes at least connector 131 and connector 132. In some embodiments, tether 130 includes additional features, such as one or more of hardware 280, IoT device 282, and sensor 283. In various embodiments, multiple instances of tether 130, which can differ, are incorporated within safety configurations associated with work area 102 to prevent user 110 from falling and/or mitigate effects of a fall.

Connector 131 and connector 132 may represent any type of connector or device known in the art that can connect one end of a tether to an anchor point or a safety harness. Connector 131 and/or connector 132 are selected based, at least in part, on a selected anchor point (e.g., a compatible mechanical configuration) and attachment points included on safety harness 270. In one embodiment, connector 131 and connector 132 are the same type or style of connector. In another embodiment, connector 131 and connector 132 differ, such as a hook and a carabiner. In some scenarios, one or more of connector 131 and connector 132 are integrated with an instance of tether 130. In other scenarios, one or more of connector 131 and connector 132 can be disconnected from an instance of tether 130, such as removed from a loop or eyelet included within tether 130 and replaced with a different type, size, and/or style of connector, such as a shackle, carabiner, maillon, etc.

Hardware 280 is representative of one or more other features or components included with some instances of tether 130, such as a quickdraw device, a figure-8 device, a shock absorber, a friction pulley or clutch, an adjustable hard-stop, an adjustable slack device etc. In some embodiments, components of hardware 280 are controlled by IoT device 282, such as changing tension applied to a friction pully or clutch, adjusting the position of a hard-stop, and modifying the length of an instance of tether 130 using an adjustable slack device until sensor 283 indicates a dictated amount of tension on tether 130.

In one embodiment, IoT device 282 is included in a smart-tether instance of tether 130. In another embodiment, IoT device 282 is incorporated within a component of hardware 280 that is attached to a standard instance of tether 130. In various embodiments, IoT device 282 includes firmware and can communicate with ASD 205 and safety harness 270 via network 290. IoT device 282 can respond to received instructions from one or more other devices and/or programs, such as safety monitoring program 400. In an embodiment, IoT device 282 utilizes information received from sensor 283 to affect one or more features of a respective tether 130. In addition, IoT device 282 can transmit information from sensor 283 to one or more other devices and/or programs via network 290.

Sensor 283 represents one or more sensors included within an instance of tether 130 or within a component of hardware 280. An instance of sensor 283 may be a strain gauge, shock (e.g., g-force) indicator, a distance sensor, or other sensor that monitors aspects of one or more components of hardware 280 and/or tether 130, such as a slack length measuring device.

In an embodiment, ASD 205 is representative of a drone or UAV. In other embodiments, an instance of ASD 205 represents another type of autonomous device that is utilized based on the nature of one or more portions of work area 102, such as an unmanned surface vehicle (USV), an unmanned underwater vehicle (UUV), a humanoid robot, a biomimicry-based robot, an application specific robot (e.g., a crawler), etc. ASD 205 includes features, such as one or more instances of camera 210, sensors 213, illumination source 215, mechanical manipulator 220, supplies 230, locomotion system 240, and system 260. In some embodiments, an instance of ASD 205 includes additional features (not shown) utilized by system 260 to control and navigate ASD 205, such as a global positioning system (GPS) receiver, a wireless communication device, a power source, etc.

In various embodiments, ASD 205 responds to commands or instructions from safety planning program 300 and/or safety monitoring program 400 to perform various actions within work area 102, such a traversing work area 102 to map work area 102, securing anchor points within area 102, attaching tether 130 to an anchor point using one or more methods, attaching tether 130 to safety harness 270, retrieving additional safety supplies, monitoring user 110, or other actions an functions described in further detail with respect to feature of ASD 205.

Camera 210 is representative of an instance of a camera utilized by ASD 205 to map a work area and monitor the movement and activities of a user. In an embodiment, ASD 205 includes two or more instances of camera 210 to enable ASD 205 to monitor (e.g., scan or image) different portions of work area 102 and/or another user 110 within work area 102. For example, a first camera 210 observes user 110 while a second camera 210 monitors ASD 205 securing an instance of anchor point within work area 102. In various embodiments, instances of camera 210 are mounted on gimbals or other electro-mechanical devices to change to orientation of camera 210 without affecting the orientation or position of ASD 205 within work area 102.

In some embodiments, some instances of camera 210 include additional capabilities, such as panoramic imaging, real-time image recording, thermal imaging, LIDAR (light detection and ranging), reflectivity, etc., that enables ASD 205 to obtain additional information related to user 110 and/or work area 102. For example, identifying an area of reduced traction (e.g., a wet area) or detecting a surface that sags as user 110 applies weight on the surface.

Sensors 213 is representative of a plurality of sensors included within an instance of ASD 205. Some sensors of sensors 213 are utilized for the navigation and control of ASD 205, such as an altimeter, an airspeed indicator, a multi-axis orientation system, a power sensor associated with locomotion system 240, etc. Other sensors of sensors 213 are associated with an instance of mechanical manipulator 220, such as a strain gauge and a torque sensor. In some embodiment, sensors 213 also include environmental sensors, such as a thermometer, a barometer, an anemometer, a moisture sensor, etc. In a further embodiment, sensors 213 includes one or more additional sensors, such as an ultrasonic sensor, an infra-red sensor, a stud detector, a current detector; or a type of sensor that can detect a structural weakness and/or previously installed elements or utilities within work area 102 and/or an anchor point.

Illumination source 215 is representative of one or more of light, visible or invisible, such as infra-red. Illumination source 215 may be adjusted to aid an instance of camera 210 to image one or more features within work area 102, such as securing an anchor point to a portion of work area 102 that is shadowed or provide a color of light for improved image recognition.

In an embodiment, mechanical manipulator 220 is a gripper-type appendage used to attach one end of an instance of tether 130 to an anchor point associated with a safety configuration utilizing an instance of connector 131. At least one instance of mechanical manipulator 220 is able to access supplies 230 to remove an item or add an item. In another embodiment, an instance of mechanical manipulator 220 can be a different type hardware for manipulating an instance of tether 130 and/or corresponding connectors 131 and 132, such as an electromagnet device. Mechanical manipulator 220 may also be able to automatically attach the other end of the instance of tether 130 to safety harness 270 utilizing an instance of connector 132. Alternatively, ASD 205 may use mechanical manipulator 220 to present the other end of the instance of tether 130 to user 110.

In some embodiments, an instance of mechanical manipulator 220 controls the actions and orientation of tools utilized by ASD 205 to create and secure (e.g., install) anchor points. In other embodiments, an instance of mechanical manipulator 220 can move an instance of camera 210, illumination source 215, and/or sensors 213 in closer proximity to a portion of work area 102 to obtain information utilized to make various determinations or identifications.

Supplies 230 includes a plurality of items utilized by ASD 205 to create and/or modify one or more safety configurations associated with a plan of tasks related to work area 102 and to ensure the safety of user 110. In one example, supplies 230 includes a supply of instances of tethers 130, a stock of a supply of instances of connectors 131 and 132, one or more tools to secure (e.g., attach) anchor points, a supply of anchor point hardware, a supply of anchor point fasteners, etc. In another example, supplies 230 includes additional items, such as instances of hardware 280 that can be attached to an instance of tether 130 and/or one or more interchangeable/configurable instances of mechanical manipulator 220.

Locomotion system 240 enables a respective instance of ASD 205 to traverse work area 102. Traversing work area 102 may include moving on work area 102, flying over work area 102, climbing around work area 102 (e.g., utilizing scaffolding), etc. In an embodiment, an instance of ASD 205 may include more than one locomotion system 240.

In an embodiment, system 260 is a computing system included within ASD 205. System 260 includes information 261, machine vision program 262, safety planning program 300, safety monitoring program 400, and other programs and data (not shown), such as a control program for ASD 205, a GPS application, a weather application, mapping or visualization software, a communication program, etc. In some embodiments, system 260 does not include sufficient computing resources and computing power to execute one or more program in near-real time. Therefore, system 260 can include client versions of machine vision program 262, safety planning program 300, and/or safety monitoring program 400 and receives information from another computing system (not shown) executing server versions of machine vision program 262, safety planning program 300, safety monitoring program 400. System 260 sends and receives information and commands via network 290.

Information 261 includes a plurality of information related to a respective user 110, an analysis of plan of tasks related to work area 102, maps of work area 102, one or more safety strategies and related safety configurations, and information associated with ASD 205. In some embodiments, information within information 261 dynamically updates as tasks are performed within work area 102 and/or a change is identified that affects work area 102 and/or user 110, such as a weather change, identifying a hazardous condition, an inventory within supplies 230, a remaining energy reserve for ASD 205, etc. In other embodiment, information 261 includes information obtained from external sources, such as the Internet, a cognitive program for predicting locations of a user based on movements of a user and/or estimates/calculates a probability of a fall based on a plurality of factors and information, safety regulations, etc.

Information within information 261 related to a respective user 110 may include biometric data, such as height, weight, reach, strength, etc.; skill information related to a task; safety preferences, such as number of tethers, confidence or lack thereof under a give set of working conditions, manual/automatic application of tether connections to safety harness 270, etc.; and communication preferences associated with device 272. Information related to a respective user 110 may be information based on user preferences, or user-provided information associated with opting-in to utilize safety planning program 300 and safety monitoring program 400.

Information within information 261 associated with a plan of tasks related to work area 102 may include: task descriptions; an order of tasks; respective locations for tasks; items (e.g., tools, fasteners, sealants, paint, etc.) utilized while perform a task; physical information related to a task, such as a size and/or weigh of an material/objects utilized during the tasks, a number of users to perform a task, etc.

Information within information 261 associated with maps of work area 102 include the information related to the plurality of items and elements previously discusses with respect to FIG. 1 (i.e., work area 102). Information 216 also includes additional information related to one or more elements or items within work area 102 determined by at least safety planning program 300 and machine vision program 262. In an embodiment, information associated with a mapped work area further includes additional information obtained from other sources, such as a blueprint, floorplan, and/or architectural drawing related to work area 102 and/or the Internet. For example, information 261 may further include traction information for sheathing and shingles with respect to various environmental conditions.

Information within information 261 associated with a safety strategy and related safety configurations may include a respective number and type of anchor points and corresponding anchor points utilized while performing a task, a number of tethers to utilize, a type of tether to utilize and respective setting for safety features included with a tether (previously discussed with respect to tether 130), an order for ASD 205 to add or move a given tether 130, navigation information associated with traversing work area 102 to perform an action or avoid obstacles.

Information within information 261 associated with an instance of ASD 205 may include configuration and capability information, related to one or more systems of features previously described with respect to FIG. 2. Information associated with an instance ASD 205 includes an inventory of items within supplies 230, a remaining energy reserve, data obtained from sensors 213, information associated with another instance of ASD 205, etc.

In an embodiment, machine vision program 262 is a suite of image processing image recognition, cognitive programs, and a database of related images for identifying items, elements, obstacles, and/or hazards within work area 102. Machine vision program 262 can operate in real-time to perform various identifications utilizing one or more instances of camera 210. Machine vision program 262 may also utilize illumination source 215 to improve imagining. In some embodiments, if machine vision program 262 cannot identify a feature or item, then machine vision program 262 utilizes system 260 to access network 290 and access another information source, such as the Internet to perform an identification and/or obtain information (e.g., weight, strength, etc.) related to an identified feature, item, or object.

In other embodiments, machine vision program 262 interfaces with one or more aspects of system 260, such as a navigation and control program (not shown) to control actions of ASD 205. In one example, system 260 utilizes machine vision program 262 to control the placement and securing of anchor points. In another example, machine vision program 262 enables safety monitoring program 400 to track the activities of user 110 while preforming tasks within work area 102 and manipulate (e.g., mover, secure, and/or unsecure) one or more instances of tether 130 to maintain the safety of user 110. In another embodiment, a server version of machine vision program 262 execute on a computing system (not shown) different from system 260.

Safety planning program 300 is a program that maps a work area, analyzes a plan of tasks related to the work area, and develops a safety strategy to improve the safety of a user (e.g., preventing and/or mitigating falls) while the user performs one or more tasks within work area 102. In one embodiment, in response to receiving a plan of tasks for work area 102 safety planning program 300 deploys one or more instances of ASD 205 to map work area 102. Subsequently safety planning program 300 analyzes the plan of tasks to be performed by a user within work area 102 based, at least in part on the mapping of work area 102, and develops a safety strategy to improve the safety of a user (e.g., prevents and/or mitigates falls) while the user performs the plan of tasks within work area 102. A safety strategy developed by safety planning program 300 includes one or more safety configurations respectively associated with a task performed by the user within work area 102. In addition, safety planning program 300 utilizes information related to user 110 to determine aspects of a safety configuration, such as the number and types of tethers to utilizes while performing a task.

Further, safety planning program 300 determines, as part of a safety strategy, a set of anchor points utilized to secure a user within work area 102. In some embodiments, if one or more dictated anchor points are not included within work area 102, then safety planning program 300 also determines the number and type of anchor points that are to be installed within work area 102 by ASD 205. In another embodiment, safety planning program 300 develops a safety strategy that includes two more users performing planned tasks, either separately or cooperatively, within work area 102. In other embodiments, safety panning program 300 executes in response to safety monitoring program 400 determining that a change to a safety configuration is needed.

Safety monitoring program 400 is a program that deploys an autonomous safety device (ASD) to a mapped work area to prepare the work area for a user to perform a set of planned tasks, instructs the ASD to implement a safety strategy within the mapped work area, monitor the work area and the user while tasks are performed, and provide active assistance to the user to prevent or mitigates falls by the user while performing the set of tasks within the mapped work area. In an embodiment, safety monitoring program 400 deploys ASD 205 to work area 102 to install a set of anchor points utilized to secure user 110 within instances of tether 130 while the user performs a task of a plan of tasks. Safety monitoring program 400 utilizes instances of ASD 205 implement a safety configuration, such as securing an end of one or more instances of tether 130 to designated anchor points and securing the other ends of instances of tether 130 to designated attachment points on safety harness 270.

In various embodiments, safety monitoring program 400 monitors the user performing a task and dynamically updates a safety configuration, such as adding or moving a tether 130 in response to the user performing a task or transitioning to a subsequent task. In some embodiments, safety monitoring program 400 can dynamically modify a safety strategy based on changes that occur within work area 102, such as the user deviating from the plan of tasks, a previously unidentified hazard is detected, and an environmental (e.g., weather change) occurs or is predicted. In other embodiments, in response to predicting a change to a safety configuration, safety monitoring program 400 can interface with an instance of safety planning program 300 to at least re-analyze a plan of tasks for work area 102 and determine another safety configuration and/or safety strategy for work area 102 based on actions of user 110, actions of other users (e.g., workers), changes within work area 102, and/or factors that affect work area 102, such as a weather change, availability of safety supplies, etc.

Safety harness 270 represents one or more pieces of safety equipment that are secured to a user 110 that instances of tether 130 can attach to user 110 to prevent a fall and/or mitigate the effects of a fall, such as reducing the impact (e.g., g-forces) experienced by the user by reducing the distance of a fall and/or slowing the rate of decent related to the fall. In an embodiment, safety harness 270 includes mechanical hardware 271, device 272, and sensors 273.

Mechanical hardware 271 includes a plurality of attachment points utilized to attach instances of connector 132 and respective instances of tether 130 corresponding to a safety configuration for user 110 and a planned task within work area 102. Attachment points may be loops, eyelets, magnetic plates, etc. In some embodiments, mechanical hardware 271 include one or more hardware items previously discussed with respect to hardware 280 of tether 130. In an embodiment, mechanical hardware 271 also includes other items utilized by user 110 to perform a task within work area 102, such as tools. In another embodiment, an item of mechanical hardware 271 can interfaces with device 272 and/or sensors 273.

In one embodiment, device 272 represents of a device of a user separate from safety harness 270, such as a cell phone, a tablet computer, or other electronic device that a user utilizes to communicate with ASD 205, safety planning program 300, and/or safety monitoring program 400. Device 272 may also include various programs and data, such as a web browser, an augmented reality (AR) application, a text messaging application, one or more communication programs, a user interface associated with ASD 205, safety planning program 300 and/or safety monitoring program 400, etc. (not shown). In another embodiment, device 272 represents a wearable device or an IoT device included within safety harness 270. Device 272 may include components, as depicted and described in further detail with respect to FIG. 5, in accordance with embodiments of the present invention.

Sensors 273 may include strain gages, a multi-axis orientation sensor, an altimeter, a GPS receiver, a vibration sensor, a temperature sensor, a weight sensor, etc.

In one embodiment, instances of ASD 205, device 272, and IoT device 282 communicate via network 290. Network 290 can be, for example, a local area network (LAN), a telecommunications network (e.g., a portion of a cellular network), a wireless local area network (WLAN), such as an intranet, a wide area network (WAN), such as the Internet, or any combination of the previous and can include wired, wireless, or fiber optic connections. In general, network 290 can be any combination of connections and protocols that will support communications between instance of ASD 205, IoT device 282 (e.g., IoT enabled tether 130), and device 272 of safety harness 270, in accordance with embodiments of the present invention. In various embodiments, network 290 operates locally via wired, wireless, or optical connections and can be any combination of connections and protocols (e.g., personal area network (PAN), near field communication (NFC), laser, infrared, ultrasonic, etc.).

Figure 3:
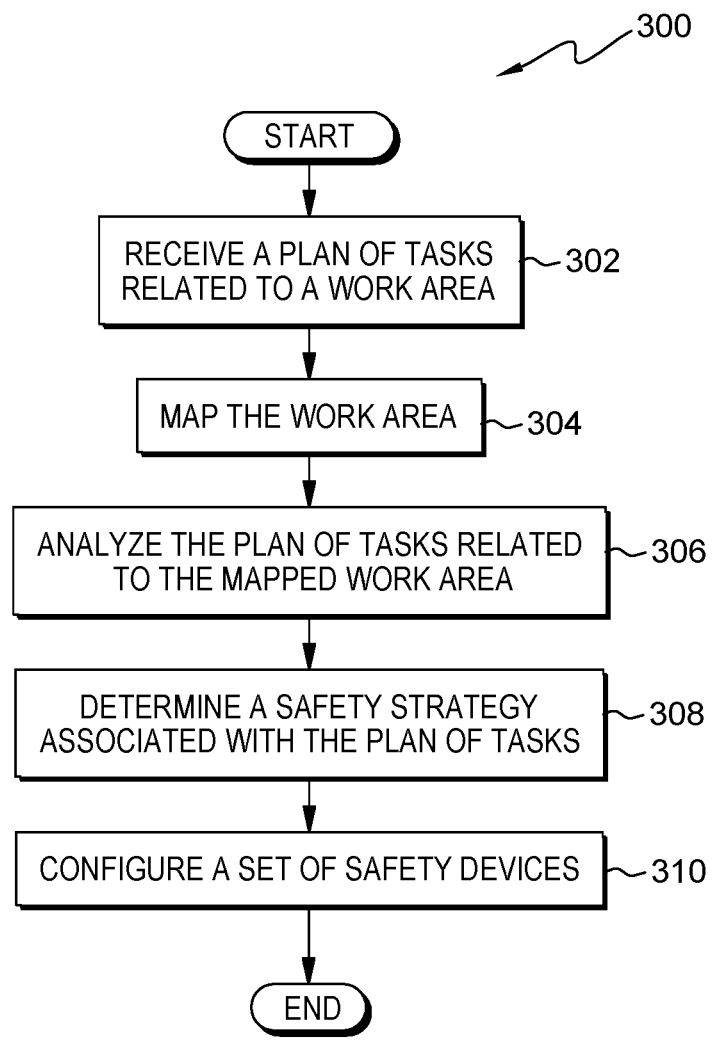
FIG. 3 depicts a flowchart of steps of a safety planning, in accordance with an embodiment of the present invention.

FIG. 3 is a flowchart depicting operational steps for safety planning program 300, a program that maps a work area, analyzes a plan of tasks related to the work area, and develops a safety strategy to improve the safety of a user (e.g., preventing and/or mitigating falls) while the user performs one or more tasks within the work area, in accordance with embodiments of the present invention. In one scenario, safety planning program 300 executes on ASD 205. In some scenarios, an instance of safety planning program 300, executing on one instance of ASD 205, cooperatively interacts with another instance of safety planning program 300 and/or safety monitoring program 400 of executing on at least one other instance ASD 205. In other scenarios, a client version of safety monitoring program 400 executes within ASD 205 and another computing device (not shown) executes server version of safety monitoring program 400. In addition, server versions of safety planning program 300 and/or safety monitoring program 400 can interact and coordinate actions among a plurality of instances of ASD 205.

In step 302, safety planning program 300 receives a plan of tasks related to a work area. Safety planning program 300 may interactively develop a plan of task related to work area 102 with user 110 and/or one or more other user. In one embodiment, safety planning program 300 receives a plan of tasks related to a work area 102 from device 272 of user 110. In another embodiment, an instance of safety planning program 300 executes offline on a computing system or device different from ASD 205 and transmits a pre-planned set of tasks for work areas 102 for storage within information 261 of one or more instances of ASD 205.

In some embodiments, an instance of system 260 within a respective instance of ASD 205 is constrained to execute a client version of safety planning program 300. Another computing device (not shown), such as on a server, laptop computer, or a different instance of ASD 205 (e.g., a master device) executes a server version of safety planning program 300 and transmits a plan of tasks for inclusion within information 261. In addition, the server version of safety planning program 300 can direct one or more actions of a respective instance of ASD 205.

In step 304, safety planning program 300 maps the work area. Mapping (e.g., surveying) work area 102 may include recoding real-time images, obtaining images (e.g., pictures) for identification and analysis, determining reference points and/or locations that are utilized to determine a plurality of 3-D positions of items within or around work area 102. In an embodiment, safety planning program 300 utilizes the plan of tasks related to work area 102 within information 261 to determine the movements or routes of one or more instances of ASD 205 utilize to map work area 102. Safety planning program 300 can utilize GPS coordinates, LIDAR, or any other positioning or measuring system known in the art to map work area 102. In some embodiments, safety planning program 300 maps work area 102 via multiple passes at differing levels accuracy and/or using differing imaging or sensing techniques. For example, safety planning program 300 instructs ASD 205 to fly, then climb to map portions of work area 102 from differing perspectives and/or resolutions.

In one embodiment, safety planning program 300 utilizes ASD 205 and at least one instance of camera 210 to map work area 102. For example, safety planning program 300 may utilize a set of panoramic cameras to obtain 360-degree images of work area 102. In another embodiment, safety planning program 300 instructs ASD 205 to also utilize one or more sensors of sensors 213 while mapping work area 102. In one example, safety planning program 300 may direct ASD 205 to use thermal or ultrasonic instances of sensors 213 to identify structural weaknesses. In another example, safety planning program 300 instructs ASD 205 to utilize mechanical manipulator 220 and a different sensor of sensor 213 to estimate the load-bearing capacity of one or more instance of element 104 within work area 102.

Still referring to step 304, in various embodiments safety planning program 300 utilizes machine vision program 262 to more precisely identify and determine information corresponding to items within work area 102. For example, safety planning program 300 utilizes machine vision program 262 to identify areas of differing traction; determine the slope of a surface; a width of an area to traverse while performing or moving between tasks; estimating the size of features/objects; identify a hazard, such as a glass as opposed to acrylic skylight; etc. In a further embodiment, a user may watch via a user interface (not shown) the mapping of work area 102 and indicate for safety planning program 300 to map other areas and/or obtain additional information related to an item within work area 102.

In step 306, safety planning program 300 analyzes the plan of tasks related to the mapped work area. In some embodiments, safety planning program 300 also utilizes maps of work area 102 and/or the received plan of tasks to determine or predict other factors that can affect user 110, such as determining size of a space that material for a task must pass through, predicting the placement of objects or materials related to other tasks that interfere (e.g., become obstacles) with a task and respective safety configuration associated with user 110, identifying areas that become more hazardous in response to a weather change, such as an area becoming a channel that funnels wind or an area of reduced traction, determining locations of supplies, determining durations to obtain one or more items for a supply location, etc.

In one embodiment, safety planning program 300 re-analyzes the plan of tasks related to work area 102 based on safety monitoring program 400 determine that user 110 deviates or is predicted to deviate from one or more tasks of plan of tasks. In another embodiment, safety planning program 300 dynamically analyzes the plan of tasks related to work area 102 based on safety monitoring program 400 predicting a change to a safety configuration based on within or external to work area 102, such as identifying an unknown hazard or a weather change.

In other embodiments, safety planning program 300 further analyzes the plan of tasks related to the map of work area 102 based additional information associated with user 110 included within information 261, such as biometric data of user 110, safety preferences, a skill level associated with performing a task; information related to a task, such as a size and a weight of material used during the task; identifying hazards and/or structural constraints included on a set of blueprints for work area 102 but undetectable by ASD 205, such as installed utilities. In response to identifying hazards and/or structural constraints, safety planning program 300 determines a plurality of exclusion zone (e.g., region) within work area 102 where one or more type of anchor points are precludes from being installed.

In step 308, safety planning program 300 determines a safety strategy associated with the plan of tasks. In an embodiment, safety planning program 300 determines a safety strategy associated with the plan of tasks based on a plurality of information, such as one or more maps of work area 102, obstacles and/or hazards that constrain movements of user 110, dictates affecting locations of one or more anchor points (e.g., avoiding previously installed utilities, structural weak points, etc.), dictates associated with the using/designating hardware or items to ensure the safety of user 110, safety preferences associated with user 110, and biometric data related to user 110, etc. For example, safety planning program 300 may designate an instance of tether 130 based on length, connectors 131 and 132, hardware 280, and/or sensor 283. A safety strategy associated with a plan of tasks related to work area 102 may include a plurality of safety configurations respectively associated with the plan of tasks; and reaction thresholds or deviation limits that trigger determining and/or utilizing an alternative safety configuration.

In one embodiment a safety configuration includes one or more inventories of supplies 230, such as types, quantities, and lengths of tethers 130; types and quantities of connector 131 and connector 132; a plurality of anchor point hardware (e.g., instance of element 103A and/or element 103B); a plurality of respective locations for instances of anchor points; whether one or more instances of element 104 are utilized; and one or more navigations routes for ASD 205. In another embodiment, a safety configuration further includes identifying potential locations for installation of instances of element 105, hardware to include within safety harness 270 and/or instances of tether 130. In some embodiments, a safety configuration also includes setting or sensor 283 value that trigger a response from a hardware 280 (e.g., a friction pulley), such as a strain gauge threshold, a slack length value, etc., associated with one or more hardware elements of safety harness 270 and/or of tethers 130.

In step 310, safety planning program 300 configures a set of safety devices. In one embodiment, safety planning program 300 notifies one or more users or instances of user 110 via device 272 or a computing device of a user (not shown), such as a tablet computer or a smartphone to manually configure a set of safety devices. Configuring a set of safety devices includes selecting instances of safety harness 270 and configuring an instance of safety harness 270 with a respective set of mechanical hardware 271, device 272, and/or sensors 273. In addition, if safety planning program 300 determines that instances of ASD 205 cannot self-configure and/or update supplies 230, then safety planning program 300 notifies user 110 and/or another user to manually prepare instances of ASD 205 with the accessories (e.g., supplies, tools, specific instances of mechanical manipulator 220) required to implement a determined safety strategy related to a plan of tasks within work area 102.

In some embodiments, safety planning program 300 activates ASD 205 and instructs ASD 205 to travel to one or more areas to self-configure and/or update supplies 230 to include items (previously discussed with respect to at least supplies 230) required to implement a determined safety strategy. In a further embodiment, if safety planning program 300 determines that one instance of ASD 205 cannot implement all the safety configurations corresponding to the tasks that user 110 is to perform, then safety planning program 300 determines to configure multiple instances of ASD 205 with the safety devices and supplies required to implement a determined safety strategy related to a plan of tasks within work area 102.

Figure 4:
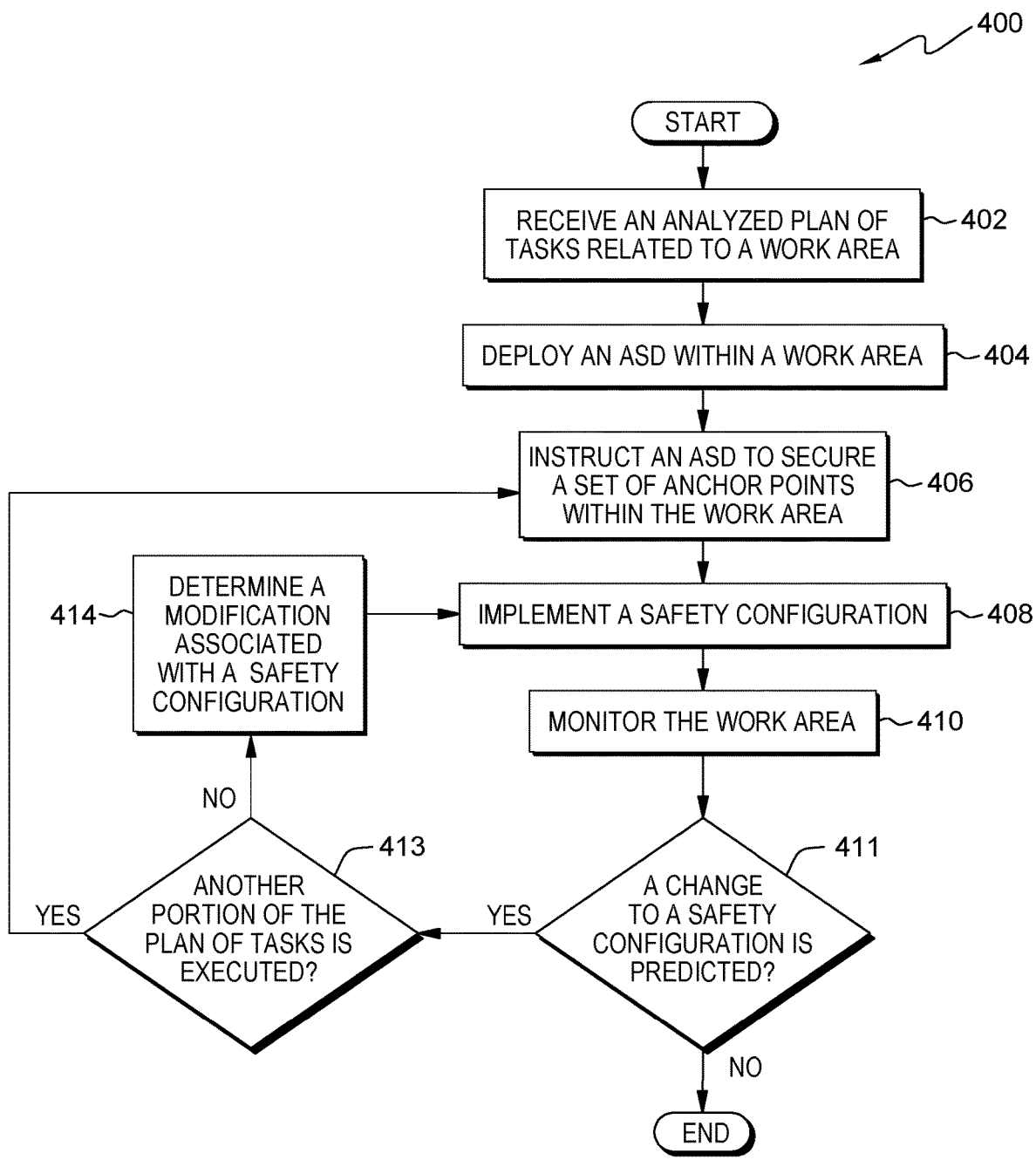
FIG. 4 depicts a flowchart of steps of a safety monitoring program, in accordance with an embodiment of the present invention.

FIG. 4 is a flowchart depicting operational steps for safety monitoring program 400, a program that monitors a work area while a user performs a task within the work area and dynamically modifies a safety configuration related to the user to ensure the safety of the user (e.g., preventing and/or mitigating a fall by the user), in accordance with embodiments of the present invention. In one scenario, safety monitoring program 400 executes on ASD 205. In some scenarios, an instance of safety monitoring program 400, executing on one instance of ASD 205, cooperatively interacts with another instance of safety planning program 300 and/or safety monitoring program 400 of executing on at least one other instance ASD 205. In other scenarios, a client version of safety monitoring program 400 executes within ASD 205 and another computing device (not shown) executes server version of safety monitoring program 400. In addition, server versions of safety planning program 300 and/or safety monitoring program 400 can interact and coordinate actions among a plurality of instances of ASD 205.

In step 402, safety monitoring program 400 receives an analyzed plan of tasks related to a work area. In one embodiment, safety monitoring program 400 receives an analyzed plan of tasks related to work area 102 from safety planning program 300. In another embodiment, safety monitoring program 400 accesses an analysis of plan of tasks related to a work area 102 from within information 261 (e.g., a pre-planned or offline developed analyses).

In step 404, safety monitoring program 400 deploys an ASD within a work area. In one embodiment, in response to user 110 entering work area 102, safety monitoring program 400 deploys ASD 205 within work area 102. In one scenario, safety monitoring program 400 deploys an instance of ASD 205 that is configured to both implement safety configurations related to tasks to be performed by user 110, and to monitor user 110 while performing a plan of tasks. In another scenario, safety monitoring program 400 deploys two or more instances of ASD 205 to implement safety configurations related to tasks to be performed by user 110 and to monitor user 110 while performing set of tasks. For example, a first instance of ASD 205 secures the anchor points utilized by a safety configuration, a second instance of ASD 205 attaches instances of tethers 130 to anchor points associated with a safety configuration and secures the tethers 130 to safety harness 270, while a third instance of ASD 205 monitors user 110 and/or one or more portions of work area 102.

In some embodiments, safety monitoring program 400 deploys multiple instances of ASD 205 within work area 102 to support two or more instances of user 110 performing a plan of tasks separately or cooperatively. In other embodiments, safety monitoring program 400 may deploy other instances of ASD 205 to resupply user 110, shuttle in a different instance of supplies 230, begin implementing a safety configuration for another task, and/or swap out an instance of ASD 205 that is running low on power with another instance of ASD 205 that has a larger or fully charged power reserve.

In step 406, safety monitoring program 400 instructs an ASD to secure a set of anchor points within the work area. In one embodiment, safety monitoring program 400 instructs ASD 205 to secure a full set of anchor points within work area 102 based on information associated with a safety strategy stored within information 261. In another embodiment, safety monitoring program 400 instructs ASD 205 to secure successive sets of anchor points within work area 102 based on information stored within information 261 and respectively associated with a safety configuration and a task to be performed by user 110. For example, safety monitoring program 400 instructs ASD 205 to secure a first set of anchor points associated with a first safety configuration for a first task of the plan of tasks. In response to determining that another portion of the plan of tasks is executed (Yes branch, decision step 413), safety monitoring program 400 instructs ASD 205 to secure a next set of anchor points respectively associated with a second safety configuration for a second task of the plan of tasks.

In some embodiments, in response to safety monitoring program 400 receiving another analysis of the plan of tasks from safety planning program 300 and/or a predicted change to a safety configuration, safety monitoring program 400 instructs ASD 205 to secure one or more other anchor points in addition to a set of anchor points that is already secured within work area 102 based on a safety configuration. In other embodiments, safety monitoring program 400 can determine to remove one or more anchor points for re-use after user 110 completes a task and one or more one or more anchor points are not utilized by a safety configuration related to another task.

In step 408, safety monitoring program 400 implements a safety configuration. In one embodiment, safety monitoring program 400 instructs ASD 205 to implement a safety configuration by attaching a designated tether 130 to a respective anchor point, then attaching the opposite end of designated tether 130 to safety harness 270. In some scenarios, a safety configuration may have a dictated order for attaching instances of tether 130 between anchor points and safety harness 270. In another scenario, in response to user 110 traversing work area 102, ASD 205 may first secure another instance of tether 130 to safety harness 270 and attach the instance of tether 130 to another anchor point when user 110 moves closer to another area associated with a task.

For example, safety monitoring program 400 implements a safety configuration that maintains a minimum of two instances of tether 130 to secure user 110. In response to user 110 approaching a movement limit, safety monitoring program 400 instructs ASD 205 to secure user 110 with another instance of tether 130, then remove the movement limiting instance of tether 130 from safety harness 270 after user the new instance of tether 130 is attached to another anchor point. Subsequently, ASD 205 detaches the limiting instance of tether 130 from the corresponding anchor point, such as an instance of element 104, and replaces limiting instance of tether 130 within supplies 230.

In some embodiments, safety monitoring program 400 implements a safety configuration by applying one or more settings or parameters to items of hardware 280 and/or mechanical hardware 271 associated with the safety configuration. In an example, safety monitoring program 400 instructs IoT device 282 of a tether 130 to set an instance of hardware 280 to a slack length of 3 feet and 5 foot-pounds of resistance on the friction pulley connected to the slack segment.

In step 410, safety monitoring program 400 monitors the work area. In one embodiment, safety monitoring program 400 utilizes one or more instances of camera 210 of ASD 205 to monitor the activities of user 110 within work area 102. Safety monitoring program 400 utilizes image recognition program 262 and a cognitive program (not shown) to determine whether user 110 is performing a task as expected, such as identifying completion of steps or actions of the task, or comparing the actions of user 110 to a video or images of previous instances of the task being performed. In various embodiments, safety monitoring program 400 utilizes two or more instances of ASD 205 to monitor different instances of user 110, observer (e.g., scan) work area 102 from multiple perspectives, inspect in-use anchor points, detect interference created by another user 110 performing a different task, etc.

In some embodiments, safety monitoring program 400 utilizes image recognition program 262 and a cognitive program to predict a new location for user 110 that deviates from the expected location of user 110 based on the steps or actions related to the task performed by user 110. In one example, if user 110 drops a tool or a piece of material associated with a task and image recognition program 262 determines that the tool or material is out of reach of user 110, then safety monitoring program 400 can predict a location and/or orientation for user 110 to retrieve the dropped tool or material. In another example, if safety monitoring program 400 determines that the user is having difficulty performing the task, then safety monitoring program 400 can predict one or more location where user 110 may move to in an attempt to perform the task, such as moving to a position to modify a portion of the material that does not fit or moving to a location away from interference from another user 110.

Still referring to step 410, in response to determining that the user deviates in one or more ways while performing a task, safety monitoring program 400 can estimate a risk or probability of a fall by the user. For example, safety monitoring program 400 predicts that user 110 will overreach to complete an action; thereby unbalancing the user and/or causing the user to stand on one, rather than two feet. In other embodiments safety monitoring program 400 utilizes one or more sensors (e.g., sensors 213, sensors 273, and/or sensor 283) to monitor user 110 and/or work area 102. For example, safety monitoring program 400 may utilize sensor data to identify excess strain (e.g., forces) on an instance of tether 130, detect a previously unknown hazard, sense wear to tether 130, determine that an anchor point is weakening, etc.

In decision step 411, safety monitoring program 400 determines whether a change to a safety configuration is predicted. In one embodiment, safety monitoring program 400 predicts a change to a safety configuration based on a user 110 completing a task of the plan of tasks related to work area 102 and that the plan of tasks includes a subsequent task. In another embodiment, safety monitoring program 400 predicts a change to a safety configuration based on a user 110 deviating from the plan of tasks related to work area 102. In one example, safety monitoring program 400 determines, based on monitoring work area 102 and/or user 110, that user 110 is performing a task differently than expected, such as a change in an order of actions related to a task. In another example, safety monitoring program 400 determines, based on monitoring work area 102 and/or user 110, that user 110 has to perform task differently than expected based on a change within work area 102, such as interference by another user 110 deviating from expectations while performing different tasks.

In some embodiments, safety monitoring program 400 predicts a change to a safety configuration based on a detecting change to work area 102 and/or receiving information from a source (not shown) external to work area 102, such as an actual or forecast change to the weather. In other embodiments, safety monitoring program 400 predicts a change to a safety configuration based on obtaining dynamic information related work area 102, such as identifying an unexpected hazard, receiving a modification to a plan of tasks, determining that the availability of one or more supplies, items of safety equipment, and/or materials is constrained. In an embodiment, safety monitoring program 400 does not predict a change to a safety configuration associated with user 110 in response to determining that the plan of task is complete and that user 110 is at a safe location within work area 102.

Responsive to determining that safety monitoring program 400 predicts a change to a safety configuration (Yes branch, Decision step 411), safety monitoring program 400 determines to determine whether another portion of the plan of tasks is executed (decision step 413).

In decision step 413, safety monitoring program 400 determines whether another portion of the plan of tasks is executed. In one embodiment, safety monitoring program 400 determines that another portion of the plan of tasks is executed based on determining that user 110 completes a task of the plan of tasks. In one scenario, safety monitoring program 400 determines that user 110 completes a task based on receiving information input by user 110 to device 272. In another scenario, safety monitoring program 400 determines that user 110 completes a task based on analyzing monitoring information associated with work area 102, such as user 110 leaving an area associated with the task, ASD 205 inspecting the area associated with the task, etc.

In another embodiment, safety monitoring program 400 determines that another portion (e.g., task) of the plan of tasks is not executed completes a task based on analyzing monitoring information associated with work area 102. For example, user 110 remaining within an area associated with the task, ASD 205 inspecting the area associated with the task, analyzing the actions of user 110 related to the task to perform, user 110 awaits a change to a safety configuration, etc.

Responsive to determining that another portion of the plan of tasks is executed (Yes branch, decision step 413), safety monitoring program 400 loops to step 406 to instruct an ASD to secure a set of anchor points within work area 102 related to the next task of the plan of tasks. If the set of anchor points related to the next task is already in installed, then safety monitoring program 400 skips to step 408 to implement a safety configuration corresponding to the next task of the plan of tasks to be performed by user 110.

Referring to decision step 413, responsive to determining that that another portion of the plan of tasks is not executed (No branch, decision step 413), safety monitoring program 400 determines a modification associated with a safety configuration (step 414).

In step 414, safety monitoring program 400 determines a modification associated with a safety configuration. In one embodiment, if safety monitoring program 400 determines that a current safety strategy does not include an alternative safety configuration related to the predicted change to a safety configuration, then safety monitoring program 400 executes or interfaces with an instance of safety planning program 300. Safety monitoring program 400 utilizes safety planning program 300 to determine at least another safety configuration to implement for the current task based on one or more changes associate with work area 102 and/or information associated with user 110. For example, safety monitoring program 400 identifies a situation or group of factors that increase the risk (e.g., probability) of falling for user 110 beyond dictated threshold (e.g., safety regulation), such as an amount of imbalance corresponding to the user. In addition, safety monitoring program 400 may instruct safety planning program to perform one or more other tasks, such as remapping a portion of work area 102 due to changes based on executing tasks or configuring additional safety devices.

In some embodiment, safety monitoring program 400 determines a modification associated with a safety configuration based on selecting from among pre-defined alternative safety configurations included within a safety strategy. In other embodiments, determines a modification associated with a safety configuration based on information within information 261, such as a preference of user 110 or a safety regulation. In one example, safety monitoring program 400 creates and installs element 105 and modifies the number of instances of tether 130 to utilize for a safety configuration in response to a condition or event, such as determining that the wind speed exceeds a threshold value. In another example, safety monitoring program 400 modifies a safety configuration based on data received from one or more of sensors 213, sensors 273, and/or sensor 283, such as detecting load forces above a threshold.

Referring to decision step 411, responsive to determining that a change to a safety configuration is not predicted (No branch, decision step 411), safety monitoring program 400 terminates.

Figure 5:
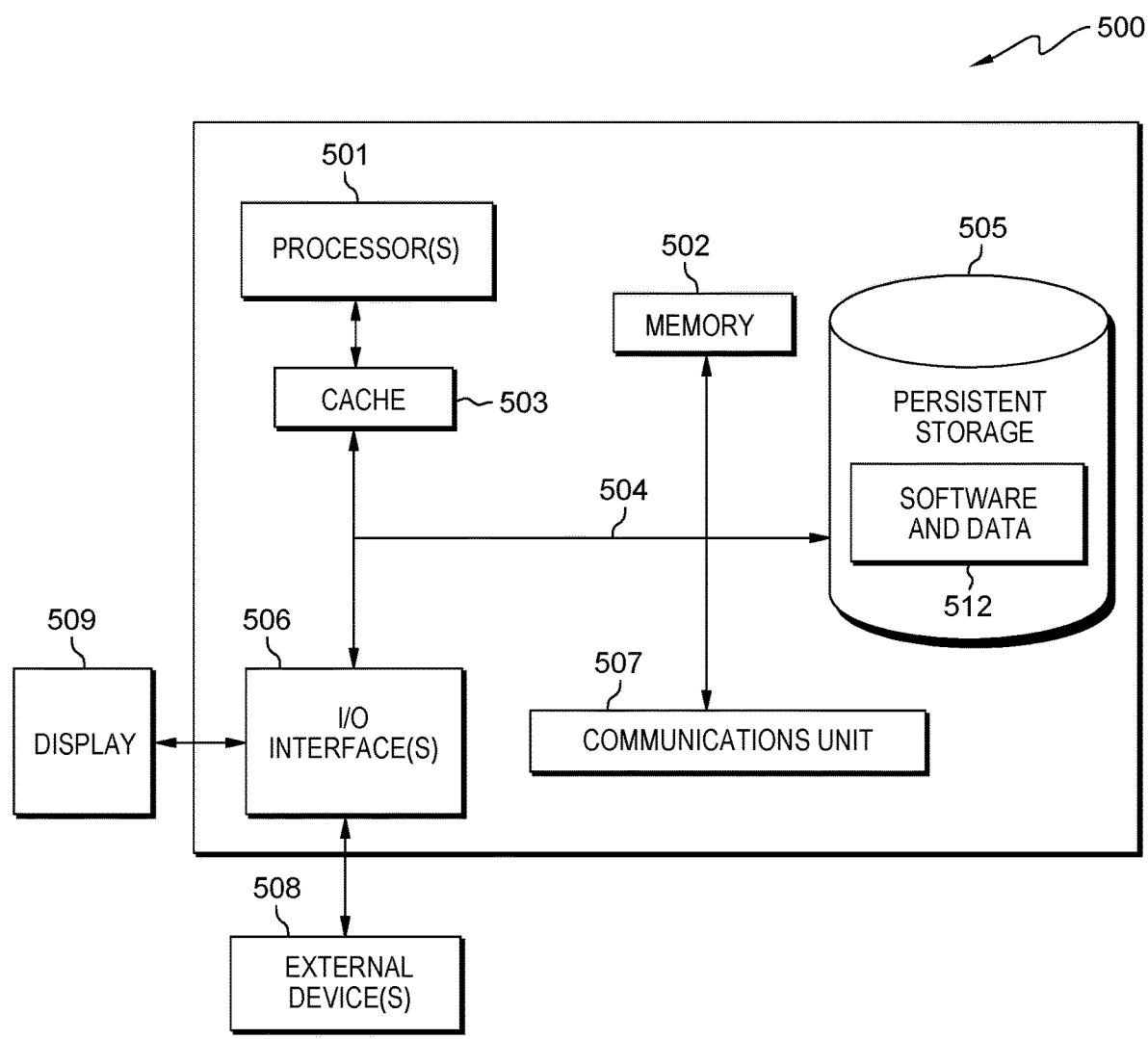
FIG. 5 is a block diagram of components of a computer, in accordance with an embodiment of the present invention.

FIG. 5 depicts computer system 500, which is representative of system 260, device 272, and IoT device 282. In some embodiments, one or more features of ASD 205 may also include one or more electronic devices and/or computing systems (not shown) that also include one or more aspects of computer system 500. Computer system 500 is an example of a system that includes software and data 512. Computer system 500 includes processor(s) 501, cache 503, memory 502, persistent storage 505, communications unit 507, input/output (I/O) interface(s) 506, and communications fabric 504. Communications fabric 504 provides communications between cache 503, memory 502, persistent storage 505, communications unit 507, and input/output (I/O) interface(s) 506. Communications fabric 504 can be implemented with any architecture designed for passing data and/or control information between processors (such as microprocessors, communications and network processors, etc.), system memory, peripheral devices, and any other hardware components within a system. For example, communications fabric 504 can be implemented with one or more buses or a crossbar switch.

Memory 502 and persistent storage 505 are computer readable storage media. In this embodiment, memory 502 includes random-access memory (RAM). In general, memory 502 can include any suitable volatile or non-volatile computer readable storage media. Cache 503 is a fast memory that enhances the performance of processor(s) 501 by holding recently accessed data, and data near recently accessed data, from memory 502.

Program instructions and data used to practice embodiments of the present invention may be stored in persistent storage 505 and in memory 502 for execution by one or more of the respective processor(s) 501 via cache 503. In an embodiment, persistent storage 505 includes a magnetic hard disk drive. Alternatively, or in addition to a magnetic hard disk drive, persistent storage 505 can include a solid-state hard drive, a semiconductor storage device, a read-only memory (ROM), an erasable programmable read-only memory (EPROM), a flash memory, or any other computer readable storage media that is capable of storing program instructions or digital information.

The media used by persistent storage 505 may also be removable. For example, a removable hard drive may be used for persistent storage 505. Other examples include optical and magnetic disks, thumb drives, and smart cards that are inserted into a drive for transfer onto another computer readable storage medium that is also part of persistent storage 505. Software and data 512 are stored in persistent storage 505 for access and/or execution by one or more of the respective processor(s) 501 via cache 503 and one or more memories of memory 502. With respect to system 260, software and data 512 includes information 261, machine vision program 262, safety planning program 300, safety monitoring program 400, and other data and programs (not shown). With respect to an instance of device 272, software and data 512 includes and other data and programs (not shown). With respect to IoT device 282, software and data 512 includes and firmware, other data, and other programs (not shown).

Communications unit 507, in these examples, provides for communications with other data processing systems or devices, including resources of system 260, device 272, and instances of IoT device 282. In these examples, communications unit 507 includes one or more network interface cards. Communications unit 507 may provide communications, through the use of either or both physical and wireless communications links. Program instructions and data used to practice embodiments of the present invention may be downloaded to persistent storage 505 through communications unit 507.

I/O interface(s) 506 allows for input and output of data with other devices that may be connected to each computer system. For example, I/O interface(s) 506 may provide a connection to external device(s) 508, such as a keyboard, a keypad, a touch screen, and/or some other suitable input device. External device(s) 508 can also include portable computer readable storage media, such as, for example, thumb drives, portable optical or magnetic disks, and memory cards. Software and data used to practice embodiments of the present invention can be stored on such portable computer readable storage media and can be loaded onto persistent storage 505 via I/O interface(s) 506. I/O interface(s) 506 also connect to display 509.

Display 509 provides a mechanism to display data to a user and may be, for example, a computer monitor. Display 509 can also function as a touch screen, such as the display of a tablet computer or a smartphone. Alternatively, display 509 displays information to a user based on a projection technology, such as virtual retinal display, a virtual display, or image projector.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random-access memory (RAM), a read-only memory (ROM), an erasable programmable read-only memory (EPROM or Flash memory), a static random-access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the invention. The terminology used herein was chosen to best explain the principles of the embodiment, the practical application or technical improvement over technologies found in the marketplace, or to enable others of ordinary skill in the art to understand the embodiments disclosed herein.

What is claimed is:

1. A method comprising:
   mapping, by one or more computer processors, a work area, wherein the work area includes a user performing a task of a plan of tasks;
   determining, by one or more computer processors, a safety configuration related to the user and the task;
   instructing, by one or more computer processors, an autonomous device to attach a first tether between a first anchor point and a safety harness secured to the user;
   analyzing, by one or more computer processors, real-time images of the work area and the user while the user performs the task;
   determining, by one or more computer processors, that the user is at risk of falling; and
   responsive to determining that the user is at risk of falling, instructing, by one or more computer processors, the autonomous device to attach a second tether between a second anchor point and the safety harness secured to the user.

2. The method of claim 1, further comprising:
   instructing, by one or more computer processors, the autonomous device to prepare the mapped work area by securing at least a first set of anchor points associated with the safety configuration.

3. The method of claim 1, wherein determining the safety configuration related to the user and the task further comprises:
   receiving, by one or more computer processors, the plan of tasks related to the work area, wherein the plan of tasks is an ordered set of tasks;
   determining, by one or more computer processors, locations corresponding to a set of anchor points utilized for respective tethers of the safety configuration; and
   determining, by one or more computer processors, a number and an order of attaching respective tethers associated with the safety configuration between the user and a corresponding anchor point based at least in part on the ordered set of tasks and the analysis of the mapped work area.

4. The method of claim 3, further comprising:
   receiving, by one or more computer processors, additional information related to the work area, the additional information includes blueprints and previously installed utilities; and
   determining, by one or more computer processors, one or more zones within the work area that precludes the installation of one or more types of anchor points.

5. The method of claim 3, wherein determining the number and the order of attaching respective tethers associated with the safety configuration between the user and the corresponding anchor point is further based on one or more preferences of the user, locations of actions related to the task, and a safety regulation.

6. The method of claim 3:
   wherein determining the number and the order of attachment for respective tethers and corresponding anchor points associated with the safety configuration is further based on one or more conditions that occurs within the work area and the task; and
   wherein the one or more conditions are selected from the group consisting of an angle of a surface related to the task, a traction value corresponding to the surface, and a width of one or more regions to be traversed while the user performs the task.

7. The method of claim 1, wherein determining that the user is at risk of falling further comprises:
   identifying, by one or more computer processors, one or more hazards, obstacles, and constraints associated with moving and utilizing material related to the task by analyzing the real-time images associated with the work area utilizing image recognition and a cognitive analysis; and
   predicting, by one or more computer processors, that the user becomes unbalanced while performing the task, wherein the risk of falling is estimated as a probability and increases based on an amount of imbalance corresponding to the user.

8. A computer program product comprising:
   one or more computer readable storage media and program instructions stored on the one or more computer readable storage media, the program instructions readable/executable by one or more computer processors:
   program instructions to map a work area, wherein the work area includes a user performing a task of a plan of tasks;
   program instructions to determine a safety configuration related to the user and the task;
   program instructions to instruct an autonomous device to attach a first tether between a first anchor point and a safety harness secured to the user;
   program instructions to analyze real-time images of the work area and the user while the user performs the task;
   program instructions to determine that the user is at risk of falling; and
   responsive to determining that the user is at risk of falling, program instruction to instruct the autonomous device to attach a second tether between a second anchor point and the safety harness secured to the user.

9. The computer program product of claim 8, further comprising:
program instructions to instruct the autonomous device to prepare the mapped work area by securing at least a first set of anchor points associated with the safety configuration.

10. The computer program product of claim 8, wherein program instructions to determine the safety configuration related to the user and the task further comprise:
program instructions to receive the plan of tasks related to the work area, wherein the plan of tasks is an ordered set of tasks;
program instructions to determine locations corresponding to a set of anchor points utilized for respective tethers of the safety configuration; and
program instructions to determine a number and an order of attaching respective tethers associated with the safety configuration between the user and a corresponding anchor point based at least in part on the ordered set of tasks and the analysis of the mapped work area.

11. The computer program product of claim 10, further comprising:
program instructions to receive additional information related to the work area, the additional information includes blueprints and previously installed utilities; and
program instructions to determine one or more zones within the work area that preclude the installation of one or more types of anchor points.

12. The computer program product of claim 10, wherein program instruction to determine the number and the order of attaching respective tethers associated with the safety configuration between the user and the corresponding anchor point is further based on one or more preferences of the user, locations of actions related to the task, and a safety regulation.

13. The computer program product of claim 10:
wherein determining the number and the order of attachment for respective tethers and corresponding anchor points associated with the safety configuration is further based on one or more conditions that occurs within the work area and the task to be performed; and
wherein the one or more conditions are selected from the group consisting of and angle of a surface related to the task, a traction value corresponding to the surface, and a width of one or more regions to be traversed while the user performs the task.

14. The computer program product of claim 8, wherein program instructions to determine that the user is at risk of falling further comprise:
program instructions to identify one or more hazards, obstacles, and constraints associated with moving and utilizing material related to the task by analyzing the real-time images associated with the work area utilizing image recognition and a cognitive analysis; and
program instructions to predict that the user becomes unbalanced while performing the task, wherein the risk of falling is estimated as a probability and increases based on an amount of imbalance corresponding to the user.

15. A computer system, the computer system comprising:
one or more computer processors;
one or more computer readable storage media; and
program instructions stored on the computer readable storage media for execution by at least one of the one or more computer processors, the program instructions comprising:
program instructions to map a work area, wherein the work area includes a user performing a task of a plan of tasks;
program instructions to determine a safety configuration related to the user and the task;
program instructions to instruct an autonomous device to attach a first tether between a first anchor point and a safety harness secured to the user;
program instructions to analyze real-time images of the work area and the user while the user performs the task;
program instructions to determine that the user is at risk of falling; and
responsive to determining that the user is at risk of falling, program instruction to instruct the autonomous device to attach a second tether between a second anchor point and the safety harness secured to the user.

16. The computer system of claim 15, further comprising:
program instructions to instruct the autonomous device to prepare the mapped work area by securing at least a first set of anchor points associated with the safety configuration.

17. The computer system of claim 15, wherein program instructions to determine the safety configuration related to the user and the task further comprise:
program instructions to receive the plan of tasks related to the work area, wherein the plan of tasks is an ordered set of tasks;
program instructions to determine locations corresponding to a set of anchor points utilized for respective tethers of the safety configuration; and
program instructions to determine a number and an order of attaching respective tethers associated with the safety configuration between the user and a corresponding anchor point based at least in part on the ordered set of tasks and the analysis of the mapped work area.

18. The computer system of claim 17 wherein program instruction to determine the number and the order of attaching respective tethers associated with the safety configuration between the user and the corresponding anchor point is further based on one or more preferences of the user, locations of actions related to the task, and a safety regulation.

19. The computer system of claim 17:
wherein determining the number and the order of attachment for respective tethers to corresponding anchor points associated with the safety configuration is further based on one or more conditions that occurs within the work area and the task; and
wherein the one or more conditions are selected from the group consisting of and angle of a surface related to the task, a traction value corresponding to the surface, and a width of one or more regions to be traversed while the user performs the task.

20. The computer system of claim 15, wherein program instructions to determine that the user is at risk of falling further comprise:
program instructions to identify one or more hazards, obstacles, and constraints associated with moving and utilizing material related to the task by analyzing the real-time images associated with the work area utilizing image recognition and a cognitive analysis; and
program instructions to predict that the user becomes unbalanced while performing the task, wherein the risk of falling is estimated as a probability and increases based on an amount of imbalance corresponding to the user.

\* \* \* \* \*